(12) United States Patent
Venus et al.

(10) Patent No.: US 7,300,670 B2
(45) Date of Patent: Nov. 27, 2007

(54) ORAL SUSPENSION FORMULATION

(75) Inventors: Danilo R. Venus, Laguna (PH);
Eulogio C. Singh, Rizal (PH); Rita Josefina M. Santos, Quezon (PH); Ma. Joyce Bedelia B. Santos, Mandaluyong (PH); Kennie U. Dee, Quezon (PH)

(73) Assignee: Unilab Pharmatech, Ltd., Central Hong Kong (CN)

( * ) Notice: Subject to any disclaimer, the term of this patent is extended or adjusted under 35 U.S.C. 154(b) by 891 days.

(21) Appl. No.: 10/115,792

(22) Filed: Apr. 3, 2002

(65) Prior Publication Data
US 2003/0191192 A1 Oct. 9, 2003

(51) Int. Cl.
*A61K 9/14* (2006.01)
*A61K 9/00* (2006.01)
(52) U.S. Cl. .............. 424/489; 424/400; 514/937
(58) Field of Classification Search ........... 424/486, 424/400, 489; 514/937
See application file for complete search history.

(56) References Cited

U.S. PATENT DOCUMENTS

| 4,607,050 A * | 8/1986 | Kieran et al. ............ 514/520 |
|---|---|---|
| 4,975,465 A | 12/1990 | Motola et al. ............ 514/557 |
| 5,112,604 A | 5/1992 | Beaurline et al. .......... 424/490 |
| 5,272,137 A * | 12/1993 | Blasé et al. ............... 514/54 |
| 5,374,659 A | 12/1994 | Gowan, Jr. ................ 514/57 |
| 5,409,907 A | 4/1995 | Blase et al. ............... 514/54 |
| 5,621,005 A | 4/1997 | Gowan, Jr. ................ 514/557 |
| 5,658,919 A | 8/1997 | Ratnaraj et al. ........... 514/269 |
| 5,712,310 A | 1/1998 | Koch ....................... 514/570 |
| 5,759,579 A | 6/1998 | Singh et al. ............... 424/485 |
| 6,231,890 B1 * | 5/2001 | Naito et al. ............... 424/489 |
| 2002/0039594 A1 * | 4/2002 | Unger ...................... 424/426 |
| 2003/0072800 A1 * | 4/2003 | Singh et al. ............... 424/464 |

OTHER PUBLICATIONS

Nakhare et al. ("Prolonged release of rifampicin from multiple W/O/W emulsion," in J. Microencapsulation, 1995, vol. 12, No. 4, 409-415).*
Pages 340 and 831 of The Condensed Chemical Dictionary, Ninth edition, 1977, edited by Hawley, Gessner G.*
Page 298 of Remington's Pharmaceutical Sciences, eighteenth edition, 1990, edited by Gennaro, Alfonso R.*
Ofner, Schnaare and Schwartz, "Oral Aqueous Suspensions." Pharmaceutical Dosage Form: Disperse Systems, vol. 2, edited by Lieberman, Ricger, and Banker, First Edition, pp. 234-236.

* cited by examiner

*Primary Examiner*—Michael G. Hartley
*Assistant Examiner*—Blessing Fubara
(74) *Attorney, Agent, or Firm*—Thomas T. Aquilla

(57) ABSTRACT

An aqueous pharmaceutical suspension for oral administration of a drug, which suspension maintains its content uniformity for prolonged period.

4 Claims, No Drawings

ORAL SUSPENSION FORMULATION

BACKGROUND OF THE INVENTION

1. Field of the Invention

The present invention relates to pharmaceutical liquid suspension formulations suitable for oral administration, more particularly to liquid suspensions that remain homogeneous during prolonged storage.

2. Description of Related Art

The most convenient and commonly employed oral drug formats are solids such as tablets and capsules. Many children and some adults however have difficulty swallowing solid dosage formats, and in this case, the drug is given in liquid form, either as syrup or suspension.

Drugs are formulated as suspensions for different reasons, but the most common one is poor drug solubility. Suspensions may also be used to mask the poor taste resulting from the dissolved drug in solution. A suspension, however, unlike syrup in which the drug is fully dissolved, requires adequate shaking of the container to resuspend the drug uniformly before dosing. Difficult redispersion of the drug from a sediment, or in the worst case, from caking, will result in under- and overdosing. This problem of variable dosing is also encountered when the patient or the caregiver forgets to shake the container before dosing. It is therefore desirable to produce a suspension that is able to maintain its homogeneity on prolonged storage without shaking.

Stoke's law defines the sedimentation rate of a sphere in a fluid as:

$$v = \frac{D^2(\rho_P - \rho_L)g}{18\mu} \quad (1)$$

where
- v=sedimentation rate
- D=mean particle diameter
- $\rho_P$=particle density
- $\rho_L$=liquid density
- g=acceleration due to gravity
- $\mu$=viscosity of the liquid phase The above equation indicates that the rate of sedimentation can be reduced by minimizing the density difference between the suspended particles and the liquid phase, reducing the particle size, and increasing the viscosity of the liquid phase.

If the densities of the suspended particle and the liquid phase are the same, sedimentation will not occur. In practice, precise matching of the densities is not always possible. The drug density may be too high, or the amount of density increasing ingredients may be too great.

Reducing the particle size is another way of slowing sedimentation. However, small particles tend to cake more severely because of the increased surface energy from the larger surface area, making redispersion much more difficult and sometimes impossible.

Small particle size is desirable for reasons other than slowing the rate of sedimentation. For drugs that are not very soluble, smaller particles generally dissolve faster due to the increase in the total surface area, which can in turn enhance bioavailability. Also, smaller drug particles are less likely to cause grittiness, which improves the palatability of the finished product. There is therefore a need for a suspension containing fine particles, hereafter referring to an average particle size less than about 20 μm, which will not cake on storage, but in addition is able to maintain its homogeneity on prolonged storage without shaking.

The most popular approach to slowing the sedimentation rate is by increasing the viscosity through the addition of a suspending agent. Excessive viscosity is undesirable, however, if it interferes with pouring and redispersal of settled particles.

As described in the book *Pharmaceutical Dosage Forms: Disperse Systems Volume* 2, Second Edition, New York, 1989, pages 234-236, yield value is an important mechanism of permanent suspensions. The theoretical yield value (Y) must balance or exceed the force of gravity on the settling particles. For spherical particles:

$$Y = \frac{2}{3\pi}(\rho_P - \rho_L)Dg \quad (2)$$

Other than providing a general guideline of introducing a yield value to the dispersion medium, this prior art is unclear on what combinations of particle size, yield value, and density difference will produce a suspension of fine particles that maintains its homogeneity for prolonged period.

The prior art has shown extensive use of combinations of suspending agents to promote redispersability. U.S. Pat. No. 4,975,465 discloses a tastemasked ibuprofen suspension comprising a suspending base of xanthan gum, microcrystalline cellulose, sodium carboxymethylcellulose and polysorbate 80. U.S. Pat. Nos. 5,272,137 and 5,409,907 teach the use of xanthan gum and microcrystalline cellulose to minimize sedimentation. U.S. Pat. Nos. 5,374,659 and 5,621,005 provide easily redispersable pharmaceutical suspensions using xanthan gum, pregelatinized starch and polyoxyethylene sorbitan monooleate. U.S. Pat. No. 5,658,919 discloses the use of xanthan gum, a mixture of microcrystalline cellulose and sodium carboxymethylcellulose, and an auxiliary suspending agent selected from hydroxyethylcellulose and a salt of carboxymethylcellulose to minimize sedimentation of paracetamol suspensions. U.S. Pat. No. 5,712,310 provides easily redispersable suspension base comprising a water-soluble modified starch, a water-soluble hydrocolloid polysaccharide, and a water-soluble wetting agent. U.S. Pat. No. 5,759,579 provides a liquid suspension base comprising xanthan gum and hydroxypropyl methylcellulose. None of these patents discloses a storage stable suspension that remains homogeneous for prolonged period of time without shaking.

U.S. Pat. No. 5,112,604 assigned to Riker laboratories discloses an aqueous pharmaceutical suspension containing large particles of coated sustained-release theophylline, wherein the drug is maintained in suspension for prolonged period. The suspending base comprises a hydrocolloid gum, colloidal silicon dioxide, a carbohydrate, and a wetting agent. This prior art does not teach how particle size, density difference, and yield value can be combined to produce a suspension of fine particles that maintains its homogeneity for prolonged period.

SUMMARY OF THE INVENTION

The present invention provides an aqueous pharmaceutical suspension for oral administration comprising at least one particulate drug with a density of from about 0.9 to about 1.6 g/ml and an average particle size of less than about 20 μm; at least one suspending polymer exhibiting plastic flow with or without additional viscosity-building agents that provides a yield value to the final suspension of about 0.2 to about 15 Pa and apparent viscosity at 100 sec$^{-1}$ of at least about 50 cps; a liquid phase with an absolute density difference from each particulate drug compound of less than about 0.2 g/ml; the final suspension being further characterized by a relative standard deviation less than 25% when tested according to the Centrifugation Test Method.

The aqueous suspension of this invention may or may not require shaking of the container prior to first use, but is able to maintain homogeneity without additional shaking for at least 30 days at room temperature. The amount of medication therefore remains uniform from dose to dose during this period.

DETAILED DESCRIPTION OF THE INVENTION

Test Methods

Test Method for Suspension Uniformity

There is no compendial USP requirement for dosage uniformity of suspension. For oral solid dosage formats, the USP requirement is that the amount of the active ingredient of each dosage unit is between 85 and 115% of label claim and the relative standard deviation of ten dosage units is less than or equal to 6.0%. We adapt this requirement with slight modifications for suspension.

A 65-ml bottle is filled with exactly 60 ml of suspension and stored for the prescribed time. Five 10-ml fractions are then carefully withdrawn from the surface of the liquid with a digital pipette (Finnpipette, Thermo Labsystems) and analyzed separately. The remaining 10 ml in the bottle, representing the sixth sample, is also analyzed. The six samples must each contain an amount of drug between 85 and 115% of label claim with a relative standard deviation (RSD) of less than or equal to 6% for the suspension to be considered uniform or homogeneous in this instant invention.

Centrifugation Test Method

A 50-ml centrifuge tube (28 mm ID×115 mm, Falcon, catalog no. 2070) is filled with exactly 50 ml of suspension and centrifuged at 450×g for 2 h at 25-30° C. Thereafter, four 10-ml fractions are carefully removed from the surface of the liquid with a digital pipette (Finnpipette, Thermo Labsystems) and analyzed separately. The remaining 10 ml in the tube, representing the fifth sample, is also analyzed. The relative standard deviation of the five samples is then calculated.

This test method is referred to as the "Centrifugation Test Method" in the instant specification and claims.

Discussion

Equation (2) above defines the minimum yield value required to prevent gravity settling or creaming. If the actual yield value (τ) is known, the acceleration required to initiate particle motion can be obtained from equation (2) simply by replacing Y with τ, and g with N×g:

$$N = \frac{3}{2}\pi \frac{\tau}{(\rho_P - \rho_L)Dg} \quad (3)$$

Where N has been expressed as number of g's. The higher the value of N, the more difficult it is to separate out the particles from the dispersion medium, i.e. the more stable the suspension. Equation (3) summarizes what is already known in the prior art with respect to improving suspension stability: smaller particle size, matching of the liquid and solid densities, and introduction of a yield value. The prior art, however, is unclear on what combination of these three factors is required to improve stability. In particular, precise matching of densities is difficult; there is a limit to particle size reduction; and very high yield value affects pourability. Also, equations 1-3 were derived by assuming monodispersed spherical particles, where in reality drug particles generally have a broad distribution, and are rarely spherical. In addition, suspensions are not always dilute and hindered settling (or creaming) must be considered. In hindered settling, the motion of a particle is affected by the presence of the neighboring particles, a phenomenon not accounted in the derivation of the above equations.

As a surrogate measure of the combined effect of particle size and its distribution, nonsphericity of the particles, yield value, hindered settling, and density difference on the stability of a suspension against particle separation, we use the RSD from the Centrifugation Test Method described previously.

The liquid pharmaceutical suspension of the present invention contains at least one particulate drug as active ingredient. The particulate drug may be partially dissolved in the liquid phase, but preferably more than about 50 percent should be particulates.

The true density of each suspended drug compound is from about 0.9 to about 1.6 g/ml, preferably from about 1.0 to about 1.4 g/ml. The allowable density range for the drug is set by the realistic density range of about 1 to 1.4 g/ml for an aqueous liquid phase, and the need to maintain the absolute density difference between the suspended drug and the liquid phase below about 0.2 g/ml.

The average particle size of the particulate drug in the present invention is less than about 20 μm, preferably less than about 15 μm, and most preferably less than about 10 μm. The fine particle size contributes to homogeneity on prolonged storage, reduced grittiness, and may enhance bioavailability in the case of poorly soluble drugs.

The liquid pharmaceutical suspension of the present invention may optionally include other dissolved drugs. The total amount of drug, both dissolved and suspended, in the composition is from about 0.02 to about 15 percent by weight, preferably from about 0.1 to about 10 percent by weight of the total composition. The suspended and dissolved drugs may be selected from but not limited to the group consisting of analgesics, decongestants, antitussives, expectorants, antihistamines, mucolytics, laxatives, vasodilators, anti-arrhythmics, anti-diarrhea drugs, anti-hypertensives, antibiotics, narcotics, bronchodilators, anti-inflammatory drugs, cardiovascular drugs, tranquilizers, antipsychotics, antitumor drugs, sedatives, antiemetics, anti-nauseants, anti-convulsants, neuromuscular drugs, hypoglycemic agents, diuretics, antispasmodics, uterine relaxants, antiobesity drugs, antianginal drugs, and antiviral drugs. Combinations of these drugs can also be used. Particular suspended drugs include but are not limited to acetaminophen, ibuprofen, and rifampicin.

One embodiment of the present invention contains the analgesic acetaminophen from about 1 to about 15 weight percent, preferably from about 1.5 to about 10 weight percent of total composition. A second embodiment of the invention contains the antibiotic rifampicin from about 0.5 to about 10 weight percent, preferably from about 1 to about 5 weight percent of total composition. Rifampicin, an antibiotic used to treat tuberculosis, is notorious for forming a very hard cake on storage that leads to bioavailability problems.

The liquid phase of the present invention has a density such that its absolute density difference from each suspended drug compound is less than about 0.2 g/ml, preferably less than about 0.1 g/ml, and most preferably less than about 0.05 g/ml. Monosaccharides, disaccharides, and sugar alcohols may be added to adjust the density of the liquid phase. If the suspension contains a suspended drug that is partially dissolved, or other dissolved drugs, the liquid density refers to the density of the liquid phase containing the dissolved drug(s). To determine the liquid density of a suspension containing dissolved drug(s), high-speed centrifugation can be used to separate the suspended drugs, and the density of the clarified liquid phase measured.

The suspension of the present invention contains at least one suspending polymer exhibiting plastic flow that imparts a yield value of about 0.2 to about 15 Pa, preferably from about 0.5 to about 10 Pa. A plastic fluid is one requiring a minimum stress (yield value) to initiate flow. When the fluid starts to flow, the apparent viscosity can remain constant (Bingham plastic) or more often drops then levels off with increasing shear rate (shear-thinning plastic). Plastic fluids can also be thixotropic where the apparent viscosity is dependent on the previous shear history. In other words, thixotropic plastic fluids need time after shearing to reform its structure and regain its yield value. Polymers exhibiting Bingham plastic and shear-thinning plastic flow are preferred. Polymers exhibiting thixotropic plastic flow can be used only if the lag time to recover 50% of the yield value is fast, less than about an hour, preferably less than about five minutes, most preferably less than about a minute. The polymer exhibiting plastic flow may be selected from but not limited to xanthan gum, carbomer, microcrystalline cellulose, carboxymethylcellulose, sodium carboxymethylcellulose, and combinations thereof. The final yield value of the suspension must be less than about 15 Pa, preferably less than about 10 Pa to ensure that the product is pourable without shaking.

In addition to a yield value, the rheology of the final suspension must have an apparent viscosity of at least about 50 cps, preferably at least about 100 cps, most preferably at least about 200 cps, at a shear rate of 100 sec$^{-1}$ to retard particle motion when the shear rate exceeds the yield value such as when shaking or pouring. For thixotropic plastic fluid, the high viscosity retards particle motion while the yield value is recovering after application of shear. When the suspending polymer(s) added to impart the yield value is not adequate to achieve the desired apparent viscosity of at least about 50 cps at a shear rate of 100 sec$^{-1}$, viscosity-building agents with no yield value can be added. These viscosity-building agents may be selected from but not limited to hydroxypropyl cellulose, hydroxypropyl methylcellulose, povidone, guar gum, locust bean gum, and combinations thereof.

The most preferred polymer in the present invention is xanthan gum from about 0.1 to about 0.5 percent by weight, most preferably from about 0.15 to about 0.4 percent by weight. Not only is xanthan gum able to provide the desired rheology without additional viscosity-building agents, it is also highly resistant to thermal degradation which ensures that the rheology does not change significantly during transport and storage in hot climates.

The suspension of the present invention is further characterized by a RSD less than about 25%, preferably less than about 12%, most preferably less than about 6% when tested according to the Centrifugation Test Method. The RSD of the Centrifugation Test Method is a surrogate measure of the combined effect of particle size and its distribution, non-sphericity of the particles, yield value, hindered settling, and density difference on the stability of a suspension against particle separation.

The aqueous suspension of the invention may or may not require shaking of the container prior to first use, but is able to maintain homogeneity without additional shaking for at least 30 days at room temperature. Whether the product requires shaking before the first use depends on the temperature history of the product prior to use. If the yield value decreases at high temperature, and no allowance is made for this temperature effect by increasing the level of the suspending polymer(s), exposure of the product to high temperature during storage may cause the product to become inhomogeneous which will then require shaking to uniformity before first use. However, after the initial shaking, the product maintains its content uniformity for at least 30 days at room temperature without additional shaking. Most often, the therapy is over or the product is consumed within 30 days. Dosage uniformity during this period ensures dosage compliance especially when the patient or caregiver forgets to shake the container everyday. Dosage uniformity is critically important for drugs with narrow therapeutic windows.

The liquid suspension of the present invention may contain additional ingredients used in the drug industry, herein referred to as additives. Additives include well-known components, but are not limited to sweetening agents, flavors, colorants, antioxidants, chelating agents, surfactants, wetting agents, antifoaming agents, pH modifiers, acidifiers, preservatives, cosolvents, and mixtures thereof.

The invention will now be described with respect to the following specific examples.

EXPERIMENT 1

This example provides an aqueous suspension containing the analgesic acetaminophen.

| Ingredient | g/100 ml |
|---|---|
| Acetaminophen (Mallinckrodt, USA) | 5 |
| Xanthan gum | 0.3 |
| Sucrose | 63 |
| Sorbitol Solution | 5 |
| Invert Sugar | 20 |
| Glycerin | 5 |
| Crospovidone (Kollidon CL-M) | 2.5 |
| Polyethylene Glycol 4000 | 0.5 |
| Sodium Benzoate | 0.2 |
| Sorbitan Monolaurate | 0.05 |
| Disodium Edetate | 0.2 |
| Sucralose | 0.2 |
| Saccharin Sodium | 0.13 |
| Citric Acid | 0.1 |
| Sodium Citrate Dihydrate | 0.295 |
| FD&C Yellow #6 | 0.006 |
| Flavor | 0.3 mL |
| Purified Water | q.s. to 100 mL |
| pH | 5–6 |

The acetaminophen suspension was prepared in the following manner:

Sucrose syrup containing sodium benzoate was prepared. The hot syrup was cooled down to 30° C. The sucrose syrup, sorbitol and invert sugar were blended together to form Phase A.

A solution of polyethylene glycol in water was prepared, and then added to Phase A. The admixture was stirred for 15 minutes to form Phase B. An aqueous dispersion of sorbitan monolaurate was prepared, and then added to Phase B to form Phase C. Crospovidone was dispersed directly into Phase C. The admixture was stirred for 30 minutes after which acetaminophen was added. The resulting admixture was stirred for one hour to form Phase D.

Xanthan gum was dispersed in glycerin, and then added to Phase D. The admixture was stirred for 15 minutes to form Phase E.

An aqueous solution of citric acid and sodium citrate dihydrate was prepared to form Phase F. An aqueous solution of disodium edetate, saccharin sodium and sucralose was prepared to form Phase G.

Phases F and G were added to Phase E. The admixture was stirred for one hour and then homogenized in a colloid mill. Color and flavor were added to the homogenized bulk then stirred for two hours before adjusting to the desired volume with water.

The following are the critical parameters of this acetaminophen suspension:

| | |
|---|---|
| Particle density @ 25° C., $\rho_P$ | 1.2904 g/ml |
| Liquid density @ 25° C., $\rho_L$ | 1.3329 g/ml |
| Absolute density difference, $|\rho_L - \rho_P|$ | 0.0425 g/ml |
| Particle size distribution: | |
| $X_{10}$ | 2.31 μm |
| $X_{50}$ (average particle size) | 8.65 μm |
| $X_{90}$ | 26.01 μm |
| $X_{99}$ | 42.21 μm |
| Rheology (25° C.): | |
| Yield Value, τ | 3–4 Pa |
| Apparent viscosity at 100 sec$^{-1}$ | 700 cps |
| Centrifugation Test results: | |
| Range of five fractions (% label claim) | 61–170 |
| RSD | 47.1% |
| Uniformity Test results: | |
| 30 Days at Room Temp. ≦30° C. | |
| Range of six fractions (% label claim) | 83–120 |
| RSD | 13.2% |

The particle density was measured using helium pycnometry (AccuPyc 1330, Micromeritics Instrument, USA), and the liquid density with a glass pycnometer (25-ml Kimax, USA). The rheology of the suspension was determined using either an Ares Rheometer (Rheometric Scientific Inc., USA) or a Haake VT550 viscometer (Haake, Germany). The particle size distribution was measured with a Helos laser diffraction analyzer (Sympatec, Germany). The particle size distribution is expressed in cumulative percentile. For example, $X_{10}$ means 10 percent of the particles has a diameter less than the indicated value.

The suspension of this example meets all the specifications of this invention except that the RSD of the Centrifugation Test is more than 25%. The suspension failed to maintain homogeneity when stored for 30 days after manufacture at room temperature without shaking.

EXPERIMENT 2

This example provides a second aqueous suspension containing the analgesic acetaminophen that meets the specifications of this invention. Note that the supplier of acetaminophen and the particle size distribution is different from Experiment 1.

| Ingredient | g/100 ml |
|---|---|
| Acetaminophen (Triton, India) | 5 |
| Xanthan gum | 0.3 |
| Sorbitol Solution | 30 |
| Invert Sugar | 35 |
| Glycerin | 5 |
| Crospovidone (Kollidon CL-M) | 2.5 |
| Polyethylene Glycol 4000 | 0.5 |
| Sodium Benzoate | 0.2 |
| Sorbitan Monolaurate | 0.05 |
| Disodium Edetate | 0.2 |
| Sucralose | 0.2 |
| Saccharin Sodium | 0.13 |
| Citric Acid | 0.1 |
| Sodium Citrate Dihydrate | 0.295 |
| FD&C Yellow #6 | 0.006 |
| Flavor | 0.3 mL |
| Purified Water | q.s. to 100 mL |
| pH | 5–6 |

The acetaminophen suspension was prepared in the following manner:

Sodium benzoate was dissolved in adequate amount of water and blended with the sorbitol and invert sugar to form Phase A.

A solution of polyethylene glycol in water was prepared, and then added to Phase A. The admixture was stirred for 15 minutes to form Phase B. An aqueous dispersion of sorbitan monolaurate was prepared, and then added to Phase B to form Phase C. Crospovidone was dispersed directly into Phase C. The admixture was stirred for 30 minutes after which acetaminophen was added. The resulting admixture was stirred for one hour to form Phase D.

Xanthan gum was dispersed in glycerin, and then added to Phase D. The admixture was stirred for 15 minutes to form phase E.

An aqueous solution of citric acid and sodium citrate dihydrate was prepared to form Phase F. An aqueous solution of disodium edetate, saccharin sodium and sucralose was prepared to form Phase G.

Phases F and G were added to Phase E. The admixture was stirred for one hour and then homogenized in a colloid mill. Color and flavor were added to the homogenized bulk then stirred for two hours before adjusting to the desired volume with water.

The critical parameters of this suspension are:

| | |
|---|---|
| Particle density @ 25° C., $\rho_P$ | 1.2951 g/ml |
| Liquid density @ 25° C., $\rho_L$ | 1.3327 g/ml |
| Absolute density difference, $|\rho_L - \rho_P|$ | 0.0376 g/ml |
| Particle size distribution: | |
| $X_{10}$ | 1.65 μm |
| $X_{50}$ (average particle size) | 5.35 μm |
| $X_{90}$ | 14.66 μm |
| $X_{99}$ | 28.14 μm |
| Rheology (25° C.): | |
| Yield Value, τ | 3–4 Pa |
| Apparent viscosity at 100 sec$^{-1}$ | 540 cps |

-continued

| Centrifugation Test results: | |
|---|---|
| Range of five fractions (% label claim) | 84–122 |
| RSD | 20.4% |
| Uniformity Test results: | |
| 90 Days at Room Temp. ≦30° C. | |
| Range of six fractions (% label claim) | 98–104 |
| RSD | 2.6% |

The suspension of this example meets all the specifications of this invention including the Centrifugation Test Method where the RSD of 20.4% is less than 25%. The suspension maintained homogeneity even when stored for 90 days after manufacture at room temperature without shaking.

EXPERIMENT 3

This example provides a third aqueous suspension containing the analgesic acetaminophen that meets the specifications of this invention. Note the same supplier of acetaminophen with the same particle size distribution as Experiment 1 was used.

| Ingredient | g/100 ml |
|---|---|
| Acetaminophen ((Mallinckrodt, USA) | 5 |
| Xanthan gum | 0.35 |
| Sucrose | 23.4 |
| Sorbitol Solution | 20 |
| Invert Sugar | 27.5 |
| Glycerin | 5 |
| Crospovidone (Kollidon CL-M) | 5 |
| Polyethylene Glycol 4000 | 0.5 |
| Sodium Benzoate | 0.2 |
| Sorbitan Monolaurate | 0.01 |
| Disodium Edetate | 0.2 |
| Citric Acid | 0.1 |
| Sodium Citrate Dihydrate | 0.56 |
| FD&C Yellow #6 | 0.006 |
| Purified Water | q.s. to 100 mL |
| pH | 5–6 |

The suspension was prepared as in Experiment 1. The critical parameters of this suspension are:

| Particle density @ 25° C., $\rho_P$ | 1.2904 g/ml |
|---|---|
| Liquid density @ 25° C., $\rho_L$ | 1.2680 g/ml |
| Absolute density difference, $|\rho_L - \rho_P|$ | 0.0224 g/ml |
| Particle size distribution: | |
| $X_{10}$ | 2.31 μm |
| $X_{50}$ (average particle size) | 8.65 μm |
| $X_{90}$ | 26.01 μm |
| $X_{99}$ | 42.21 μm |
| Rheology (25° C.): | |
| Yield Value, τ | 4–5 Pa |
| Apparent viscosity at 100 sec$^{-1}$ | 900 cps |
| Centrifugation Test results: | |
| Range of five fractions (% label claim) | 99–101 |
| RSD | 0.6% |
| Uniformity Test results: | |
| 12 months at Room Temp. ≦30° C. | |
| Range of six fractions (% label claim) | 94–106 |
| RSD | 3.3% |

The suspension of this example meets all the specifications of this invention including the Centrifugation Test Method where the RSD of 0.6% is much less than 25%. The suspension maintained homogeneity even when stored for 1 year after manufacture at room temperature without shaking.

EXPERIMENT 4

A commercial product Children's Tylenol Flu (Lot EEM 096, McNeil-PPC, USA) containing per 5 ml: 160 mg suspended acetaminophen, 1 mg dissolved chlorpheniramine maleate, 7.5 mg dissolved dextromethorphan hydrobromide, and 15 mg dissolved pseudoephedrine hydrochloride was tested. The listed ingredients of this suspension suggest that it is formulated according to U.S. Pat. No. 5,658,919 using xanthan gum, a mixture of microcrystalline cellulose and sodium carboxymethylcellulose, and a salt of carboxymethylcellulose as suspending agents. The product comes in 120-ml bottles. After shaking vigorously, 60 ml of product was transferred to a 65-ml bottle, shaken vigorously again and stored for seven days without additional shaking before subjecting to the "Uniformity Test".

The particle density of acetaminophen from Experiment 1 was used. The liquid density was determined by measuring the density of the liquid phase after centrifugation at 1000× g's for 2 h to remove the suspended particles (microscopic examination of the liquid phase after centrifugation indicated complete removal of suspended particles). Approximate particle size distribution of the suspended drug was determined by microscopy.

The results are as follows:

| Particle density @ 25° C., $\rho_P$ | 1.2904 g/ml |
|---|---|
| Liquid density @ 25° C., $\rho_L$ | 1.2276 g/ml |
| Absolute density difference, $|\rho_L - \rho_P|$ | 0.0628 g/ml |
| Approx. particle size distribution: | |
| <20 μm | 20% |
| 21–50 μm | 10% |
| 51–100 μm | 10% |
| >100 μm | 60% |
| Rheology (25° C.): | |
| Yield Value, τ | <5 Pa |
| Apparent viscosity at 100 sec$^{-1}$ | 185 cps |
| Centrifugation Test results: | |
| RSD | >100%* |
| Uniformity Test results: | |
| 7 Days at Room Temp ≦30° C. | |
| Range of six fractions (% label claim) | 91–112 |
| RSD | 7.8% |

*physical separation; significant amount of particles settling

This example shows that even if the densities of the solid and liquid phase are closely matched, the product still failed to maintain homogeneity during a short storage period of seven days at room temperature. The product does not meet the particle size and Centrifugation Test RSD specifications of the present invention and therefore is outside the scope of the present invention.

EXPERIMENT 5

A commercial product Children's Motrin Oral Suspension (Lot CPM060, McNeil-PPC, USA) containing 100 mg suspended ibuprofen per 5 ml was tested. The box label claims that the suspension was formulated according to U.S. Pat. No. 5,374,659 using xanthan gum, pregelatinized starch, and polyoxyethylene sorbitan monooleate as suspending agents.

The product comes in 120-ml bottles. After shaking vigorously, 60 ml of product was transferred to a 65-ml bottle, shaken vigorously again and stored for seven days without additional shaking before subjecting to the "Uniformity Test".

The particle density of ibuprofen was determined from a commercially available raw material (Albermarle, USA). The liquid density was determined by measuring the density of the liquid phase after centrifugation at 1000×g's for 2 h to remove the suspended particles (microscopic examination of the liquid phase after centrifugation indicated complete removal of suspended particles). Approximate particle size distribution was determined by microscopy.

The results are as follows:

| | |
|---|---|
| Particle density @ 25° C., $\rho_P$ | 1.1158 g/ml |
| Liquid density @ 25° C., $\rho_L$ | 1.1283 g/ml |
| Absolute density difference, $\|\rho_L - \rho_P\|$ | 0.0125 g/ml |
| Approx. Particle size distribution: | |
| <20 µm | 15% |
| 21–50 µm | 20% |
| 51–100 µm | 25% |
| >100 µm | 40% |
| Rheology (25° C.): | |
| Yield Value, τ | <5 Pa |
| Apparent viscosity at 100 sec$^{-1}$ | 90 cps |
| Centrifugation Test results: | |
| RSD | >100%* |
| Uniformity Test results: | |
| 7 Days at Room Temp ≦30° C. | |
| RSD | 8.8% |

*physical separation; significant amount of particles creaming

This example shows that even if the densities of the solid and liquid phase are closely matched, the product still failed to maintain homogeneity during a short storage period of seven days at room temperature. The product does not meet the particle size and Centrifugation Test RSD specifications of the present invention and therefore is outside the scope of the present invention.

EXPERIMENT 6

This example provides an aqueous suspension containing the antibiotic rifampicin.

| Ingredient | Example 6-A g/100 ml | Example 6-B g/100 ml |
|---|---|---|
| Rifampicin (Ciba-CKD, India) | 4 | 4 |
| Xanthan gum | 0.1 | 0.2 |
| Invert Sugar | 55 | 55 |
| Sorbitol Solution | 20 | 20 |
| Glycerin | 5 | 5 |
| Sodium Benzoate | 0.2 | 0.2 |
| Polysorbate 80 | 0.01 | 0.01 |
| Sodium metabisulfite | 0.1 | 0.1 |
| Simethicone | 0.05 | 0.05 |
| Saccharin Sodium | 0.1 | 0.1 |
| Flavor | 0.6 | 0.6 |
| Purified Water | q.s. to 100 ml | q.s. to 100 ml |

One liter of each suspension was prepared in the following manner:

Sodium benzoate and saccharin were dissolved in adequate amount of water and added to invert sugar and sorbitol. The blend was mixed and then vacuumed at −28" Hg for 15 minutes to form Phase A.

Sodium metabisulfite was dissolved in an adequate amount of water, and polysorbate 80 dispersed in another portion of water. Both were added to Phase A, then mixed to form Phase B.

The rifampicin powder was slowly added to Phase B with stirring, homogenized for 15 minutes, then vacuumed at −28" Hg for 2 h. Simethicone was then added with stirring to form Phase C.

Xanthan gum was dispersed in glycerin and added to Phase C and mixed for 15 minutes. The strawberry flavor was added and then water to make up to the desired volume. The mixture was further vacuumed at −28" Hg for 1 h to give the final suspension.

The critical parameters of these two formulations are as follows:

| | Example 6-A | Example 6-B |
|---|---|---|
| Particle density @ 25° C., $\rho_P$ | 1.2750 g/ml | 1.2750 g/ml |
| Liquid density @ 25° C., $\rho_L$ | 1.2853 g/ml | 1.2935 g/ml |
| Absolute density difference, $\|\rho_L - \rho_P\|$ | 0.0103 g/ml | 0.0185 g/ml |
| Particle size distribution: | | |
| $X_{10}$ | 0.40 µm | 0.40 µm |
| $X_{50}$ (average particle size) | 1.72 µm | 1.72 µm |
| $X_{90}$ | 5.44 µm | 5.44 µm |
| $X_{99}$ | 9.85 µm | 9.85 µm |
| Rheology (25° C.): | | |
| Yield Value, τ | 0.3 Pa | 0.6 Pa |
| Apparent viscosity at 100 sec$^{-1}$ | 58 cps | 120 cps |
| Centrifugation Test results: | | |
| Range of five fractions (% label claim) | 76–118 | 97–104 |
| RSD | 18.7% | 2.6% |
| Uniformity Test results: | | |
| 30 Days at Room Temp. ≦30° C. | | |
| Range of six fractions (% label claim) | 95–107 | 98–102 |
| RSD | 4.6% | 1.0% |

Both examples are within specifications of the present invention and both are homogenous when stored for 30 days after manufacture at room temperature without shaking. Note that the lower the RSD of the Centrifugation Test, the lower the RSD of the product on storage.

EXPERIMENT 7

This example provides an aqueous suspension containing the antibiotic rifampicin. Note the source of the active and its particle size distribution is different from Example 6. The particles in this experiment are larger than in Experiment 6.

| Ingredient | Example 7-A g/100 ml | Example 7-B g/100 ml |
|---|---|---|
| Rifampicin (Gujarat, India) | 4 | 4 |
| Xanthan gum | 0.1 | 0.2 |
| Invert Sugar | 55 | 55 |
| Sorbitol Solution | 20 | 20 |
| Glycerin | 5 | 5 |

-continued

| Ingredient | Example 7-A g/100 ml | Example 7-B g/100 ml |
|---|---|---|
| Sodium Benzoate | 0.2 | 0.2 |
| Polysorbate 80 | 0.01 | 0.01 |
| Sodium metabisulfite | 0.1 | 0.1 |
| Simethicone | 0.05 | 0.05 |
| Saccharin Sodium | 0.1 | 0.1 |
| Flavor | 0.6 | 0.6 |
| Purified Water | q.s. to 100 ml | q.s. to 100 ml |

The suspensions were prepared as in Experiment 6. The critical parameters are:

| | Example 7-A | Example 7-B |
|---|---|---|
| Particle density @ 25° C., $\rho_P$ | 1.2764 g/ml | 1.2764 g/ml |
| Liquid density @ 25° C., $\rho_L$ | 1.2853 g/ml | 1.2935 g/ml |
| Absolute density difference, $|\rho_L - \rho_P|$ | 0.0089 g/ml | 0.0171 g/ml |
| Particle size distribution: | | |
| $X_{10}$ | 0.68 μm | 0.68 μm |
| $X_{50}$ (average particle size) | 3.21 μm | 3.21 μm |
| $X_{90}$ | 11.28 μm | 11.28 μm |
| $X_{99}$ | 20.83 μm | 20.83 μm |
| Rheology (25° C.): | | |
| Yield Value, τ | 0.3 Pa | 0.6 Pa |
| Apparent viscosity at 100 sec$^{-1}$ | 71 cps | 110 cps |
| Centrifugation Test results: | | |
| Range of five fractions (% label claim) | Physical separation* | 94–104 |
| RSD | >50% | 2.6% |
| Uniformity Test results: | | |
| 30 Days at Room Temp. ≦30° C. | | |
| Range of six fractions (% label claim) | 77–125 | 98–101 |
| RSD | 22.2% | 1.4% |

*significant amount of particles creaming

Example 7-A does not meet RSD Centrifugation Test specification of the present invention, and failed to maintain uniformity when stored for 30 days after manufacture at room temperature. Example 7-B, with a higher yield value that lowered the Centrifugation Test RSD, meets all the specifications of the current invention and maintained product homogeneity when stored for 30 days after manufacture at room temperature without shaking.

EXPERIMENT 8

This example provides an aqueous suspension containing the antibiotic rifampicin. Note the source of the active and its particle size distribution is different from Experiments 6 and 7, the particles in this experiment being larger.

| Ingredient | g/100 ml |
|---|---|
| Rifampicin (Lupin, Thailand) | 4 |
| Xanthan gum | 0.3 |
| Invert Sugar | 55 |
| Sorbitol Solution | 20 |
| Glycerin | 5 |
| Sodium Benzoate | 0.2 |
| Polysorbate 80 | 0.01 |
| Sodium metabisulfite | 0.1 |
| Simethicone | 0.05 |
| Saccharin Sodium | 0.1 |
| Flavor | 0.6 |
| Purified Water | q.s. to 100 ml |

Forty liters of the suspension was prepared in a PVM 10 Mixer (Charles Ross & Son, USA). The PVM 10 is a liquid processing vacuum mixer with a marine impeller stirrer, and a rotor-stator homogenizer, both of which can be operated under vacuum. The PVM 10 has been modified with a powder feed tube feeding directly into the homogenizer so the active can be added with the homogenizer operating under vacuum to prevent air entrainment.

The suspension was prepared as follows:

Sodium benzoate and saccharin were dissolved in adequate amount of water and added to invert sugar and sorbitol in the mixer. A vacuum of −22" Hg was pulled, and then the stirrer turned on. Mixing continued for 30 minutes under vacuum to form Phase A.

Sodium metabisulfite was dissolved in an adequate amount of water, and polysorbate 80 dispersed in another portion of water. The mixer was opened, and both solutions added to Phase A. The mixer was then closed, vacuum pulled to −22" Hg, and the stirrer turned on for 10 minutes while maintaining vacuum to form Phase B.

The rifampicin powder was slowly added to the closed mixer through the feed tube, with the homogenizer and stirrer operating under a vacuum of −22" Hg. After adding all the Rifampicin, mixing and homogenization under vacuum continued for 90 minutes. The mixer was then opened, simethicone added, mixer closed, vacuum pulled to −22" Hg, and stirrer turned on for 10 minutes to form Phase C.

The mixer was opened and xanthan gum dispersed in glycerin was added to Phase C. The mixer was then closed, vacuum pulled to −22" Hg, and both stirrer and homogenizer turned on for 20 minutes. The mixer was again opened, strawberry flavor added, and then water added to make up to the desired volume. The mixer was closed, vacuum pulled to −22" Hg, and the stirrer turned on for 15 minutes under vacuum to give the final suspension.

The critical parameters of this suspension are as follows

| Particle density @ 25° C., $\rho_P$ | 1.2760 g/ml |
|---|---|
| Liquid density @ 25° C., $\rho_L$ | 1.2873 g/ml |
| Absolute density difference, $|\rho_L - \rho_P|$ | 0.0113 g/ml |
| Particle size distribution: | |
| $X_{10}$ | 2.5 μm |
| $X_{50}$ (average particle size) | 7.24 μm |
| $X_{90}$ | 16.35 μm |
| $X_{99}$ | 30.09 μm |
| Rheology (25° C.): | |
| Yield Value, τ | 1.9 Pa |
| Apparent viscosity at 100 sec$^{-1}$ | 310 cps |
| Centrifugation Test results: | |
| Range of five fractions (% label claim) | 97–105 |
| RSD | 2.9% |
| Uniformity Test results: | |
| Initial RSD | 4.4% |
| 14.2 months at Room Temp. ≦30° C. | |
| Range of six fractions (% label claim) | 97–105 |
| RSD | 3.1% |

The suspension meets the specifications of the present invention and maintained product homogeneity when stored for 14.2 months after manufacture at room temperature without shaking.

To determine if xanthan gum at the level used provides enough allowance against: temperature effects, fresh samples were stored at 40° C. for six months and the critical parameters evaluated.

|  | Fresh Sample Before storage | 6 mo at 40° C. Unshaken | 6 mo at 40° C. Shaken* |
|---|---|---|---|
| Particle size distribution (microscopy) | Reference | No change | No change |
| Uniformity Test results: |  |  |  |
| Range of six fractions (% label claim) | 95–108 | 77–149 | 99–101 |
| RSD | 4.4% | 25.6% | 1.0% |
| Centrifugation Test results: |  |  |  |
| Range of five fractions (% label claim) | 97–105 | — | 93–106 |
| RSD | 2.9% | — | 4.7% |

*a mother was asked to shake the bottle as she would normally shake a suspension On storage for six months at 40° C., product homogeneity changed significantly, from an RSD of 4.4% to more than 25%. However, on shaking the container, product homogeneity was recovered. Further, the product, which was stored for six months at 40° C. and then shaken, passed the Centrifugation Test with an RSD<6%. When the product, stored for six months at 40° C. and then shaken to homogeneity, was stored at room temperature without additional shaking, the following results were obtained:

| Uniformity Test results: | Initial | 30 Days at Room Temp. | 60 days at Room Temp. |
|---|---|---|---|
| Range of six fractions (% label claim) | 99–101 | 97–105 | 97–104 |
| RSD | 1.0% | 2.5% | 2.9% |

Clearly, the suspension of this example contains enough xanthan gum that even when the product has been subjected to a temperature of 40° C. for six months, as long as the product is shaken to homogeneity and subsequently stored at room temperature, the product is able to maintain its uniformity for up to 60 days without additional shaking.

EXPERIMENT 9

This example provides another aqueous suspension containing the antibiotic rifampicin.

| Ingredient | g/100 ml |
|---|---|
| Rifampicin (Gujarat, India) | 4 |
| Xanthan gum | 0.35 |
| Invert Sugar | 55 |
| Sorbitol Solution | 20 |
| Glycerin | 5 |
| Sodium Benzoate | 0.2 |
| Polysorbate 80 | 0.01 |

-continued

| Ingredient | g/100 ml |
|---|---|
| Sodium metabisulfite | 0.1 |
| Simethicone | 0.05 |
| Saccharin Sodium | 0.1 |
| Flavor | 0.6 |
| Purified Water | q.s. to 100 ml |

The suspension was prepared as in Experiment 8. The critical parameters of this suspension are as follows:

| Particle density @ 25° C., $\rho_P$ | 1.2764 g/ml |
|---|---|
| Liquid density @ 25° C., $\rho_L$ | 1.3020 g/ml |
| Absolute density difference, $|\rho_L - \rho_P|$ | 0.0256 g/ml |
| Particle size distribution: |  |
| $X_{10}$ | 0.68 μm |
| $X_{50}$ (average particle size) | 3.21 μm |
| $X_{90}$ | 11.28 μm |
| $X_{99}$ | 20.83 μm |
| Rheology (25° C.): |  |
| Yield Value, τ | 2.7 Pa |
| Apparent viscosity at 100 sec$^{-1}$ | 400 cps |
| Centrifugation Test results: |  |
| Range of five fractions (% label claim) | 95–103 |
| RSD | 3.0% |
| Uniformity Test results: |  |
| 14.1 months at Room Temp. ≦30° C. |  |
| Range of six fractions (% label claim) | 95–108 |
| RSD | 4.5% |

The suspension meets the specifications of this invention and maintains its uniformity when stored at room temperature without shaking for 14.1 months.

A transport test was conducted to determine the effect of shear on the uniformity of the product. Several boxes (144 bottles/box) of 6-month old unshaken samples were loaded into a delivery van and transported across 350-km of mixed smooth roads and rough terrains. A bottle from each box was then assayed for content uniformity.

Representative assays are as follows:

| Uniformity Test results: | Bottle 1 | Bottle 2 | Bottle 3 |
|---|---|---|---|
| Range of six fractions (% label claim) | 95–114 | 98–104 | 97–106 |
| RSD | 5.4% | 2.2% | 3.8% |

The results indicate that content uniformity was maintained against the shear stress induced during transport.

A simulated consumer use test was also conducted on this suspension. For this test, 128-ml bottles containing 120 ml of product were used. The bottles were either stored at room temperature for five months or for four months at 40° C. before use. Bottles stored at 40° C. were cooled to room temperature overnight before the test.

At day one of the test, mothers were asked to shake the bottles as they would normally shake suspensions before dosing. A 10-ml sample was then poured out of a bottle for chemical assay. Thereafter, 10-ml samples were poured out of the same bottle (without shaking) everyday for ten days, with the remaining 10 ml in the bottle representing the twelfth dose. All bottles were stored at room temperature during the test.

The results of replicate experiments are as follows:

| Uniformity Test results | Replicate 1 | Replicate 2 |
|---|---|---|
| Product stored for 5 months at ≦30° C.: | | |
| Range of 12 fractions (% label claim) | 95–105 | 98–102 |
| RSD | 3.3% | 1.8% |
| Product stored for 4 months at 40° C.: | | |
| Range of 12 fractions (% label claim) | 99–102 | 98–102 |
| RSD | 1.1% | 2.0% |

The results indicate that content uniformity is maintained in a test simulating actual use, i.e. shaking only on the first dose, and then no shaking until the content of the bottle is consumed.

EXPERIMENT 10

A commercial rifampicin suspension in the Philippines, Rifamax (Glaxo), containing 200 mg of active per 5 ml was tested. The particle density of rifampicin was determined from a commercially available raw material (Gujarat, India). The liquid density was determined by measuring the density of the liquid phase after centrifugation at 1000×g's for 2 h to remove the suspended particles (microscopic examination of the liquid phase after centrifugation indicated complete removal of suspended particles). Approximate particle size distribution was determined by microscopy.

The critical parameters of this suspension are:

| | |
|---|---|
| Particle density @ 25° C., $\rho_P$ | 1.2764 g/ml |
| Liquid density @ 25° C., $\rho_L$ | 1.1830 g/ml |
| Absolute density difference, $\|\rho_L - \rho_P\|$ | 0.0934 g/ml |
| Approx. particle size distribution: | |
| <10 μm | 10% |
| 11–40 μm | 20% |
| 41–80 μm | 30% |
| 81–100 μm | 20% |
| >100 μm | 20% |
| Rheology (25° C.): | |
| Yield Value, τ | 2.3 Pa |
| Apparent viscosity at 100 sec$^{-1}$ | 38 cps |
| Centrifugation Test results: | |
| Range of five fractions (% label claim) | Physical separation |
| RSD | >200% |
| Uniformity Test results: | |
| 24 h at Room Temp. ≦30° C. | Sediments with clear interface |

This suspension does not meet the specifications of the present invention, and fails to maintain uniformity 24 hours after shaking.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

We claim:

1. An aqueous rifampicin suspension comprising from about 1 to about 5 percent by weight rifampicin with an average particle size less than about 10 μm; from about 0.1 to about 0.5 percent by weight of xanthan gum; from about 0.01 to about 2 percent by weight of at least one antifoaming agent; from about 0.001 to about 0.5 percent by weight of at least one wetting agent; a liquid phase with an absolute density difference of less than about 0.05 g/ml from the particulate rifampicin; the suspension being further characterized by a relative standard deviation of less than about 6% when tested according to the Centrifugation Test Method.

2. The suspension according to claim 1, wherein the antifoaming agent is present at about 0.02 to about 0.2 percent by weight.

3. The suspension according to claim 1, wherein the wetting agent is present at about 0.005 to about 0.2 percent by weight.

4. The suspension according to claim 1, further comprising one or more additives selected from the group consisting of sweetening agents, flavors, colorants, antioxidants, chelating agents, viscosity-building agents, surfactants, pH modifiers, acidifiers, preservatives, cosolvents, and mixtures thereof.

* * * * *